United States Patent [19]

Bryce-Smith

[11] Patent Number: 5,688,532
[45] Date of Patent: Nov. 18, 1997

[54] ANTIALLERGIC SPRAY PREPARATIONS

[75] Inventor: Derek Bryce-Smith, Reading, England

[73] Assignee: Kappa Pharmaceuticals Limited, Reading, England

[21] Appl. No.: 357,776

[22] Filed: Dec. 16, 1994

Related U.S. Application Data

[63] Continuation of Ser. No. 115,571, Sep. 1, 1993, abandoned, which is a continuation of Ser. No. 882,112, May 13, 1992, abandoned, which is a continuation of Ser. No. 555,272, Jul. 19, 1990, abandoned.

[30] Foreign Application Priority Data

Jul. 20, 1989 [GB] United Kingdom ............ 8916625

[51] Int. Cl.$^6$ .................... A61K 33/32; A61K 31/315
[52] U.S. Cl. ........................... 424/641; 514/4.94
[58] Field of Search .................. 514/494; 424/641

[56] References Cited

U.S. PATENT DOCUMENTS 4,503,070  3/1985  Eby, III .................. 514/494

OTHER PUBLICATIONS

C.D. Weir, Intranasal Ionization in the Treatment of Vasomotor Nasal Disorders, pp. 1143–1149 (1931).

Lionel D. Bailey C.B., M.C., M.R.C.S., and Clive Shields, B.M., B. Ch., Treatment of Hay Fever by Intranasal Zinc Ionization, The British Medical Journal, Apr. 17, 1937, p. 808.

H. Hilton Stewart, M.D., M.R.C.P. and J.H. Biggart, M.B., B. Ch., A Case of Acute Bronchiolectasis The British Medical Journal, Jun. 27, 1931, pp. 1115–1116.

Clive Shields, B.M., B.Ch., The Ionization Treatment of Hay Fever, The Practitioner, pp. 645–648 (1931).

Defination of "Hay–Fever" from Hutchinson's 20th Century Encyclopedia, p. 597 (1960).

Primary Examiner—Zohreh Fay
Attorney, Agent, or Firm—Oblon, Spivak, McClelland, Maier & Neustadt, P.C.

[57]  ABSTRACT

The present invention provides a simple, cheap and efficient treatment for an allergic condition, especially hay-fever or asthma, and comprises a nasal, oral or ophthalmological spray of a dilute solution of, preferably substantially unchelated, zinc ion, especially zinc sulfate and/or zinc chloride.

13 Claims, No Drawings

ANTIALLERGIC SPRAY PREPARATIONS

This application is a continuation of application Ser. No. 08/115,571, filed on Sep. 1, 1993 now abandoned, which is a continuation of application Ser. No. 07/882,112, filed on May 13, 1992 now abandoned, which is a continuation of application Ser. No. 07/555,272, filed on Jul. 19, 1990 now abandoned.

FIELD OF THE INVENTION

The present invention relates to preparations of zinc compounds for use in the treatment and/or prophylaxis of allergic conditions.

DISCUSSION OF THE ART

Zinc and its compounds have long been recognized as possessing certain therapeutic functions. Particularly well recognized are their benefits as astringents and wound healing agents. The later use tends to be restricted to zinc chloride and zinc sulfate, zinc chloride being of use for application to foul-smelling wounds and ulcers, while zinc sulfate is given internally to promote healing.

Zinc sulfate has also proven beneficial in the treatment of *acrodermatitis enteropathioa* and, in common with zinc acetate, is used in eye drops, optionally in combination with adrenaline or boric acid (no longer medically recommended), to relieve chronic inflammation of the cornea in conjunctivitis. Together with zinc chloride, zinc sulfate is also used as an astringent mouth wash, and was formerly used as a reflex emetic, owing to its irritant and adverse effects on the gastro-intestinal mucosae (of Merck Index, entry 9966).

Zinc compounds have also been used, with varying degrees of success, in the treatment of acne, aphthous ulcers, coeliac disease, cystic fibrosis, senile dementia, furunculosis, gastric ulcers, hyperthyroidism leg ulcers, porphyria, rheumatoid arthritis, sickle-cell anaemia and ulcerative colitis. Marone et al. (Agents and Actions [1986], 18, 103–6) describe the in vitro antihistamine activity of zinc on mast cells, while Walker et al. (Search [1975], 6, 134–5) describe the recovery of mice suffering from anaphylactic shock after an injection of zinc compound.

Recently, investigation of zinc compounds has centred upon their possible use to inhibit or cure the common cold. For example, Eby, et al. (Antimicrobial Agents and Chemotherapy [1984], 25, (1), pp 20–24) disclose the use of zinc gluconate lozenges in the treatment of the common cold. Although their study indicated that around 86% of zinc-treated subjects were asymptomatic after treatment, compared with only 46% of placebo-treated subjects, observers noted "objectionable taste and mouth irritation" in the patients. Zinc gluconate was used, as any more ionic compound would have been likely to result in violent and undesirable side-effects.

In any event, interest in the use of zinc gluconate has dwindled as, with one exception, attempts to duplicate Eby's results have been uniformly negative. In addition, Eby's original results were questioned, given that, as noted above, zinc ions taste metallic and cause a sore mouth and nausea in the patient. In addition, the Merck Index (10th Edition) notes that zinc compounds are irritating to both the skin and to mucous membranes, and states that a solution of zinc sulfate has a pH of 4.5. For a review of results obtained with zinc gluconate, see Antimicrobial Agents and Chemotherapy (1988), 32, pp. 605–7.

In U.S. Pat. No. 4,503,070, Eby discloses the use of nasal sprays of zinc gluconate solutions to treat the common cold, but such use is not only unsupported by the description, but the concentrations specified are of an order of magnitude so large as to cause substantial discomfort to the patient.

Later, Eby established that a zinc gluconate nasal spray (10 mM) was only marginally effective, and was not worth following up. Further, DE 3 431 727 A1, filed in 1984, discloses a nasal spray comprising zinc gluconate in a 2% solution. No results are provide, and the applicant failed to continue with the application.

In two other papers in Antimicrobial Agents and Chemotherapy ([1987], 31, 1183–7 and 1263–5), it was established that neither zinc gluconate nor zinc acetate provided a therapeutically useful treatment of rhinovirus colds.

Co-pending EP-A-0 381 522 discloses a nasal spray of substantially unchelated zinc ions for the treatment and prophylaxis of the common cold.

SUMMARY OF THE INVENTION

It is an object of the present invention to provide cheap and effective preparations useful against allergic conditions and which do not have any noticeable side-effects.

It is a further object to provide an effective preparation against asthma and hay-fever.

Thus, in accordance with a first aspect of the present invention, there is provided a method for the treatment or prophylaxis of allergic conditions, in a subject in need thereof, comprising administering a non-toxic solution of zinc ion, preferably substantially unchelated, in the form of a spray to the eyes or to the respiratory tract of the subject, especially by the nasal route.

In another aspect, there is provided the use of an ionic zinc compound in the manufacture of a medicament for the treatment or prophylaxis of an allergic condition by spraying the medicament into the eyes or respiratory tract, the medicament comprising a solution containing ionic zinc, preferably unchelated.

In a yet further aspect, there is provided an aerosol dispensing device, preferably hand-held, comprising a reservoir of a, preferably aqueous, solution containing ionic zinc, preferably substantially unchelated, the device being adapted to dispense a spray of the solution into a human nostril or eye for the purpose of the treatment or prophylaxis of an allergic condition.

DETAILED DESCRIPTION

Not only have we now established that it is possible to use even fully ionic preparations of zinc in amounts which are effective without any noticeable side-effects, but we have also established that zinc ion-containing sprays are effective in the treatment and prophylaxis of allergic conditions, an area which has not previously been explored with regard to zinc, despite the number of other uses it is, or has been, put to.

In particular, we have discovered that a solution containing zinc ion, administered in the form of a spray to the respiratory tract, nasally or orally, or to the eyes, is effective in the treatment or prophylaxis of allergic conditions, especially asthma and hay-fever, attacks of which may be either avoided or reduced, depending on the stage at which treatment is effected. A cure, or substantial relief of symptoms, may frequently be effected even during substantial attacks.

It is particularly surprising that the sprays of the present invention should be so efficacious against asthma and hay-fever, as such a use for zinc compounds has not been suggested previously. However, the action of zinc ions in this capacity may possibly be associated with the inhibition of uncontrolled secretion of histamines by mast cells in allergic conditions. Accordingly, depending on the condition, it may be preferable to apply the solution by way of the nasal or the oral cavity, it generally being preferable to use the oral cavity for asthma or a sore throat, while use of the nasal cavity in the case of hay-fever or a cold is usually preferred, although severe symptoms may benefit from application via both nasal and oral cavities, and relief will usually be available even when a route other than that recommended is used. Sore eyes, or eyes with conjunctivitis, may particularly benefit from being sprayed in accordance with the invention.

The term 'ionic', as used herein, relates to suitable zinc compounds capable of use to give solutions of ionic zinc.

we generally prefer that the zinc ion is substantially unchelated, although this is not a requirement. Essentially, although we do not wish to be bound by theory, it is likely that it is free zinc which exerts the advantageous effects of the invention, and so it is desirable to ensure the maximum amount of free zinc.

By the term 'allergic condition' is meant any condition associated with non-infectious external factors which have an adverse effect on the individual. Such conditions are typified by hay-fever and asthma, but also include allergy to house dust and chemical food additives. Essentially, the sprays of the present invention are particularly of use where any heterologous, or foreign, factor stimulates overproduction of histamines, thereby causing inconvenience and discomfort to the victim.

The treatments of the present invention may possibly only be of use in suppressing the symptoms associated with the relevant allergic conditions, but results tend to be both prompt and dramatic. Symptoms which may be alleviated, or cured, include itchy eyes, shortness of breath, headaches, sore throat, runny and/or congested nose and coughs.

The terms 'treatment' and 'prophylaxis' are used in a broad sense, and extend from purely symptomatic relief, to cure of the condition, and to general preventative therapy, especially in season, or for particularly prone individuals.

It is unlikely that the preparations of the invention exert an effect other than on, for example, inflamed tissue, and do not affect either the source of the irritation or the propensity of the body to respond to the irritants. However, the advantages of alleviating the symptoms are enormous, and such relief can considerably enhance the quality of lie of the sufferer, especially the chronic sufferer.

However, it may be the case that an effective cure may be provided, either through prolonged treatment or by making up what may be a zinc deficiency. Prolonged treatment may have the effect of reducing or banishing the hypersensitivity associated with the instant conditions, while provision of zinc ion from an exogenous source may make up any short term deficiency, and the natural tendency of zinc to bind bodily tissue can help to extend the duration of relief.

The preparations of the invention are suitable for use prophylactically or any time from when the subject first notices any signs of an allergic condition until the symptoms have cleared up. In fact, in some case, such as for persistent sufferers, or where individually desired, it may be appropriate to continue treatment indefinitely, in the absence of contraindications.

In general, best results seem to be obtained when treatment is commenced immediately there is any suspicion of onset of an allergic reaction. Several doses in rapid succession, such as between 2 and 10, preferably about 4 to 6 over an hour, are frequently sufficient to overcome even the most severe attack. If symptoms persist after this initial period, it is generally recommended to reduce frequency of dosing to the levels described hereunder.

By 'substantially unchelated' is meant any solution of zinc ion wherein a majority of the zinc is in free ionic solution. As stated above, it is desirable, but not essential, that the zinc is substantially unchelated.

Any compound may be used that releases zinc ion in solution, preferably with a dissociation constant allowing a concentration of between 1 and 100% in deionized water of zinc to bound zinc. Certain compounds may ordinarily provide solutions of chelated zinc but, provided that some zinc present is ionic, may still be usable, especially where the solvent chosen effectively prevents chelation, or where the chelating moiety is somehow prevented from chelating the zinc totally. It may also be the case that the final solution contains amounts of zinc chelator. This will not generally present a problem, especially where the chelator is present in less than, preferably very much less than, stoichiometric amounts, compared to zinc. In such cases, it may be necessary to calculate the amount of chelated zinc and to subtract this from the total before calculating dosages.

Thus, in contrast to the art, wherein it has previously been considered that solutions of free ionic zinc could not be administered at all, and especially not in effective doses, without giving rise to substantial irritation and other adverse side effects, we have discovered that patients treated with the sprays of the invention report no bad taste or other side effects.

By 'solution' is meant any solution of ionic zinc suitable to provide free zinc ion on administration. Although the invention extends to solutions of zinc capable of yielding free zinc ion but which contain zinc in another form, it is generally the case that preferred solutions contain substantially unchelated zinc ion.

Thus, despite the strong contraindications in the art regarding the medical use of zinc, it has been found that it is possible to use ionic zinc solutions in low enough concentrations that no irritation is caused, but in high enough concentrations to be effective. In fact, zinc compounds, especially zinc sulfate, are generally only recommended for clinical use in concentrations of less than 0.25%. The sprays of the invention are effective at concentrations of 0.1% or lower, whereas those solutions, including sprays, described in the art are around 2%, and are not disclosed for use in the field of antiallergics.

In treatment, it is generally preferred to administer the spray via the nasal cavity, although someone may benefit from application via both nasal cavities, and often the eyes as well.

Efficacy is probably also enhanced by the affinity of zinc ions for mucous tissues. Thus, zinc ion is still present in the affected areas for periods of up to several hours after administration.

A particular advantage of the invention is that considerably less zinc compound, in terms of orders of magnitude, is required for efficacy, and no irritation, metallic taste or other undesirable side-effects are observed, and the solutions are remarkably effective, even at low concentrations.

In addition, the solutions of the invention are desirably sufficiently dilute that there is no problem with acidity. A 0.1% solution of zinc sulfate heptahydrate in deionized water typically has a pH of 5.1, for example, rising to about 5.7 after boiling to drive off carbon dioxide. This is similar to unpolluted rainwater.

Particularly good results have been obtained with zinc sulfate, although other ionic zinc compounds can be used, especially the chloride. In general, suitable anions are those allowing free dissociation in solution, that is, which do not chelate the zinc ion. Those compounds of low solubility, or which are only soluble with difficulty, may be less convenient for use, but are not excluded from the invention provided that an effective concentration of zinc may be obtained.

Generally preferred compounds are salts of the mineral acids. Inorganic or simple organic compounds, such as zinc acetate, are generally preferable. Less preferable are compounds which are capable of chelating zinc, such as the gluconate or citrate.

It will also be appreciated that a compound dissolved in a solution of another compound will not necessarily yield a solution exhibiting the expected characteristics. For example, zinc chloride dissolved in a carbonate solution is likely to precipitate zinc carbonate, thereby reducing or eliminating zinc in solution.

The solvent used to dissolve the ionic zinc compounds may be selected from any that is physiologically acceptable. Zinc sulfate, for example, is virtually insoluble in alcohol, but freely soluble in water, while zinc chloride is soluble in either. Indeed, a direct aqueous solution of the compound forms a preferred embodiment. However, other solutions are equally preferred, such as those based on saline and/or aqueous glycerol, or other mixtures suitable for nasal or ophthalmological administration.

In tests, an aqueous solution of zinc sulfate has proven particularly effective, while zinc sulfate in saline is apparently not quite so effective, although test parameters varied somewhat, and the sue of saline may be preferably to render the spray solution isotonic with tears or the nasopharyngeal environment. Persistence and severity of the attack may be of significance with regard to efficacy, but attacks treated even at later stages have responded well.

The solutions used in accordance with the invention may also contain other ingredients that may be considered desirable, generally provided that these do not give rise to unduly high levels of chelation. Useful ingredients include, for example, buffering agents, flavor and/or odor enhancing agents, surface active agents, dispersing agents, decongestants and the like. The solutions for use in accordance with the invention may also contain, or be combined with, other medications suitable for administration by nasal or ophthalmological spray, such as antimicrobial agents and antihistamines, especially vitamin C, or ascorbate.

One preferred nasal preparation contains about 0.1% menthol and about 3% ethanol (to dissolve the menthol). Such a formulation is preferred for the reason that a straight solution of zinc is virtually unnoticeable, especially when the patient suffers nasal discharge, and menthol, or another suitable compound, such as camphor, serves to make the patient aware of the presence of the solution, thereby preventing inhalation of an unnecessarily large dose which could, of itself, prove irritating.

The solutions of the invention may contain the ionic zinc compound in any suitable concentration. However, it is generally preferable to administer the compound in a concentration of between 0.01 and 1%, with 0.05 to 0.3% being particularly preferred. Solutions in excess of −1% are increasingly liable to cause some irritation of mucous membranes.

The solution of the invention is preferably administered in doses of about 0.05 to 0.5 ml, more preferably 0.2 ml, per nostril. Administration to the eye is preferably in the lower range, but the eye may be flooded if desired or prescribed, although frequent flooding may lead to irritation through excess levels of zinc.

Administration is as often as required, but two does per nostril at approximately six-hourly intervals has proven effective. The eye may be treated as often as itching is noted, or in accordance with a regimen, such as described above. Other regimens will be clear to those skilled in the art.

If the subject has a runny or blocked nose, it is generally recommended that they blow their nose before administration, to facilitate access of the solution to the mucosae. In such cases, repeat spraying within a period of 30 minutes or less may be desirable. Inhaling during spraying is also recommended.

The solutions of the invention may be prepared in any suitable manner. In general, this will involve no more than the dissolution of the compound in the solvent at ambient or elevated temperature, and preferably under aseptic conditions.

Suitable aerosol dispensers for use in accordance with the invention will be apparent to those skilled in the art, and may vary from simple devices analogous to perfume dispensers to pressurized spray cans and even complex apparatus such as might be used in hospitals.

Whichever device is used it is generally preferable that it comprises some kind of dosimeter to control the amount of solution administered in one go. A preferred device, which corresponds to a perfume dispenser with a nozzle, effectively incorporates, by design, such a dosimeter without any specialized adaptation being necessary, the limit stop of the depressable spray head fixing the maximum single amount of solution dispensed in one shot. An ophthalmological device may further incorporate a shield to prevent undue and inconvenient spraying of the rest of the face.

Specially developed spray devices may be made, but is generally preferable to provide a simple hand-held device comprising a reservoir of the zinc solution. Suitable means for dispensing the spray, preferably in aerosol form, are then provided. Examples include devices employing pressurized gas forced across the opening of a tube leading into the reservoir to create an aerosol, and press-button type devices wherein the button, when pressed, creates pressure on the surface of the liquid in the reservoir, forcing it up through a tube and through a fine nozzle to disperse the solution into an aerosol spray.

It is generally preferable that air forms the aerosol propellant, but any physiologically acceptable propellant may be use.

The following Example is for illustration only, and is not to be construed as limiting the invention in any way.

EXAMPLE 1

Hay-fever and Asthma

A preparation of zinc solution (0.1%) was made up in deionized water and placed in individual hand dispensers. Patients having various symptoms of allergic conditions, ranging from virtually asymptomatic through to streaming nose etc., were offered the dispensers.

The initial does comprised 2 sprays per nostril, each spray being about 02. ml. The one administration was generally sufficient to effect total relief and 6-hourly doses offered continuing relief from symptoms.

In each case, rapid relief was afforded, and the subjects were able to remain substantially asymptomatic for so long as administration was continued. In some case, the asymptomatic condition endured for prolonged periods even in the absence of treatment.

What is claimed is:

1. A method for the treatment of an allergic condition, said method consisting essentially of spraying a solution comprising a non-toxic, anti-allergy effective amount of ionic zinc to the eye or respiratory tract of a mammal possessed of said allergic condition at a concentration below that which causes irritation to mucus membranes, the majority of said ionic zinc in said spray being unchelated zinc and in the form of free ionic solution, wherein said solution has a zinc ion content of between about 0.002 to about 0.12% (w/v).

2. The method of claim 1, wherein said allergic condition is selected from the group consisting of hay-fever and asthma.

3. The method of claim 1, wherein said solution is selected from the group consisting of essentially aqueous and essentially saline solutions.

4. The method of claim 1, wherein said solution has a zinc ion content of about 0.04% (w/v).

5. The method of claim 1, wherein said solution comprising a mineral acid salt of zinc as solute.

6. The method of claim 1, wherein said solution comprises a solute selected from the group consisting of zinc sulfate and zinc chloride.

7. The method of claim 1, wherein said spray is dispensed in aliquots.

8. The method of claim 7, wherein said aliquots are about 0.05 to about 0.5 ml.

9. The method of claim 7, wherein said aliquots are about 0.2 ml.

10. The method of claim 1, wherein said solution further comprises at least one other pharmaceutically acceptable ingredient.

11. The method of claim 10, wherein said further ingredient is selected from the group consisting of antihistamines, scenting agents and active ingredients.

12. The method of claim 10, wherein said further ingredient comprises ascorbate.

13. In a method for the treatment of an allergic condition by the administration of a zinc compound to a mammal possessed of an allergic condition, the improvement consisting essentially of:

spraying a solution comprising a non-toxic, anti-allergy effective amount of ionic zinc to the eye or respiratory tract of a mammal possessed of said allergic condition, said solution comprising a concentration of ionic zinc below that which causes irritation to mucus membranes, the majority of said ionic zinc in said spray being unchelated zinc and in the form of free ionic solution, wherein said solution has a zinc ion content of between about 0.002 to about 0.12% (w/v).

* * * * *